United States Patent [19]

Yamataka et al.

[11] 4,414,079

[45] Nov. 8, 1983

[54] PROCESS FOR THE PREPARATION OF A 4-BUTANOLIDE COMPOUND

[75] Inventors: Kazunori Yamataka; Toshiro Isoya; Nobuya Kitaguchi, all of Nobeoka, Japan

[73] Assignee: Asahi Kasei Kogyo Kabushiki Kaisha, Osaka, Japan

[21] Appl. No.: 398,604

[22] Filed: Jul. 15, 1982

[30] Foreign Application Priority Data

Sep. 30, 1981 [JP] Japan ................... 56-155746

[51] Int. Cl.$^3$ ............................... C25B 3/00
[52] U.S. Cl. .................... 204/75; 549/295; 204/59 R
[58] Field of Search .............. 204/72, 59 R, 73 R, 204/75

[56] References Cited

U.S. PATENT DOCUMENTS 3,630,861 12/1971 Bizot ........................... 204/72

OTHER PUBLICATIONS

Shono et al., Tetrahedron Letters, vol. 21, pp. 5029–5032 (1980).
Tomilov et al., Zh. Org. Khim., vol. 11, No. 9, 1984–1985 (1975).

Primary Examiner—John F. Niebling
Attorney, Agent, or Firm—Armstrong, Nikaido, Marmelstein & Kubovcik

[57] ABSTRACT

The electrolytic reduction of a mixture of an acrylic ester and an aldehyde in the form of an aqueous emulsion in the presence of at least one phase-transfer catalyst using a lead or lead alloy cathode has been found to be very effective for preparing a 4-butanolide compound simply and safely in high yield with a high current efficiency.

20 Claims, No Drawings

PROCESS FOR THE PREPARATION OF A 4-BUTANOLIDE COMPOUND

This invention relates to a process for the preparation of a 4-butanolide compound. More particularly, the present invention is concerned with a process for the preparation of a 4-butanolide compound from a mixture of an acrylic ester and an aldehyde by electrolytic reduction which enables the desired product to be obtained simply and efficiently. The term "4-butanolide compound" as used herein is intended to mean 4-butanolide ($\gamma$-butyrolactone) and 4-substituted 4-butanolides.

4-Butanolides, especially 4-alkyl-4-butanolide are widely used as perfumes for foods and cosmetics because of their peculiar aroma and are also useful as intermediates in the syntheses of perfumes, pharmaceuticals, agricultural chemicals and the like. For example, 4-n-propyl-4-butanolide has a cumarin-like aroma while 4-n-hexyl-4-butanolide has a nut-like aroma in concentrated solution and a peach-like aroma in dilute solution, and, therefore, they have been highly appreciated in the perfume industry.

To produce 4-butanolides, there have hitherto been proposed various methods. Conventionally, 4-butanolides are produced, for example, by reduction of $\gamma$-ketonic acid; hydrolysis of $\gamma$-halo acid; and condensation of an aliphatic aldehyde with malonic acid in the presence of an alkaline catalyst to form a $\beta,\gamma$-unsaturated carboxylic acid, followed by treatment of the resulting $\beta,\gamma$-unsaturated carboxylic acid with diluted sulfuric acid or the like to effect cyclization thereof. There has also been proposed a method in which a mixture of an acrylic ester and a primary alcohol is heated in the presence of di-tert-butyl peroxide. However, $\gamma$-ketonic acid, $\gamma$-halo acid and malonic acid are not only poor in availability but also expensive. Therefore, the conventional methods in which such acids as mentioned above are used as starting materials are disadvantageous from a practical point of view. With respect to the method in which di-tert-butyl peroxide is used, not only expensive is the peroxide but also a special care should be taken in carrying out the reaction in order to avoid explosion of the reaction system during the course of the reaction in which the instable peroxide participates and which should be carried out at a high temperature.

There are also known other methods of producing 4-butanolides in which an acrylic ester is coupled with an aldehyde by electrolytic reduction in a homogeneous system containing the reactants. For example, "Tetrahedron Letters", vol. 21, 5029–5032(1980) discloses a method of producing a 4-butanolide compound in which a homogeneous system comprising an acrylic ester, an aldehyde, trimethylchlorosilane, an electrolyte and dimethylformamide as a solvent is subjected to electrolytic reduction using the cathode made of lead to form the intended 4-butanolide compound. However, this method has many disadvantages as follows. In this method, a large amount of expensive solvent, dimethylformamide, should be employed so that a reaction system comprising an acrylic ester, an aldehyde and an electrolyte may be kept to be homogeneous. Further, trimethylchlorosilane used in this method is also expensive. This expensive trimethylchlorosilane should be employed in an amount equimolar to that of the aldehyde used and a special care should be taken in handling trimethylchlorosilane because trimethylchlorosilane is readily hydrolyzed by the action of moisture in air. In addition, since not only the electrolytic reduction is carried out in a homogeneous system but also the solubility of dimethylformamide in water is great, extremely complicated procedures are required to separate the desired product and to recover the electrolyte from the homogeneous reaction mixture. Furthermore, a great amount of heat is required to distill off a large amount of the solvent used. As is apparent from the foregoing, the method disclosed in "Tetrahedron Letters", vol. 21, 5029–5032(1980) is disadvantageous for industrial practice.

On the other hand, "Zh. Org. Khim.", vol. 11, No. 9, 1984–1985(1975) discloses a method of producing 4-butanolides in which a mixture of acetaldehyde and propionaldehyde is subjected to a coupling reaction with an acrylic ester in aqueous potassium phosphate by electrolytic reduction using a graphite electrode activated by means of mercury. However, the graphite electrode used in this method is difficult to prepare. Moreover, because of a poor mechanical strength of the electrode, the electrode often undergoes breakage or crazing when installed in a filter press-type electrolytic cell commonly used on a commercial scale, which leads to leakage of mercury and causes environmental pollution. Furthermore, in this method, complicated procedures are required to separate and purify the desired product produced because 4-butanolides produced are a mixture of 4-methyl-4-butanolide and 4-ethyl-4-butanolide. For the reasons as mentioned above, the method disclosed in "Zh. Org. Khim.", vol. 11, No. 9, 1984–1985(1975) is not regarded as being advantageous for producing 4-butanolides.

The present inventors have made extensive and intensive studies with a view to eliminating the above-mentioned drawbacks of the conventional methods for producing 4-butanolides and to providing a process for the preparation of a 4-butanolide compound by which a 4-butanolide compound can be produced simply and efficiently on a commercial scale. As a result, the present inventors have found that a 4-butanolide compound can be produced simply and safely in high yield with a high current efficiency by subjecting to electrolytic reduction a mixture of an acrylic ester and an aldehyde in the form of an aqueous emulsion comprising a water phase and an organic phase in the presence of at least one phase-transfer catalyst selected from the group consisting of quaternary ammonium salts and quaternary phosphonium salts in an electrolytic cell provided with a lead or lead alloy electrode as the cathode. The present inventors have further found that a 4-butanolide compound produced by the above-mentioned process can be easily separated from the reaction system and the phase-transfer catalyst employed can also be easily separated from the reaction system and recovered for reuse. The present invention has been made based on such novel findings.

Therefore, it is an object of the present invention to provide a process for the preparation of a 4-butanolide compound in which a 4-butanolide compound can be produced from readily available starting materials by electrolytic reduction simply and safely in high yield with a high current efficiency.

Other objects and advantages of the present invention will become apparent from the detailed description to follow taken in conjunction with the appended claims.

In accordance with the present invention, there is provided a process for the preparation of a 4-butanolide compound which comprises subjecting a mixture of an acrylic ester and an aldehyde to electrolytic reduction, said mixture of the acrylic ester and the aldehyde being in the form of an aqueous emulsion comprising a water phase and an organic phase, in the presence of at least one phase-transfer catalyst selected from the group consisting of quaternary ammonium salts and quaternary phosphonium salts in an electrolytic cell provided with at least one pair of anode and cathode, said cathode being made of lead or a lead alloy.

In general, the reaction of an acrylic ester with an aldehyde by electrolytic reduction can be shown by the following reaction formula:

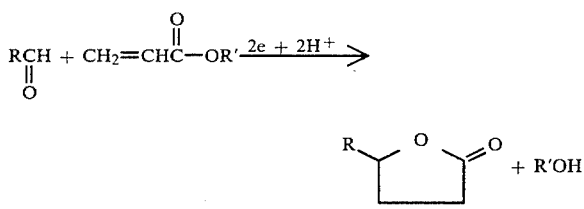

wherein R stands for hydrogen atom or such a group as substituted or unsubstituted alkyl group, substituted or unsubstituted aryl group, substituted or unsubstituted aralkyl group, substituted or unsubstituted alkenyl group, or substituted or unsubstituted alkynyl group and R' such a group as alkyl group.

In the present invention, it is requisite that the reaction system comprising an acrylic ester and an aldehyde be subjected to electrolytic reduction in the form of an aqueous emulsion comprising a water phase and an organic phase. As mentioned before, the method in which an acrylic ester is reacted with an aldehyde by electrolytic reduction in a homogeneous system has various drawbacks. More detailed explanation will be given below. In the conventional method for producing 4-butanolides by subjecting an acrylic ester and an aldehyde to electrolytic reduction in a homogeneous system, there is used as a reaction medium a mixed solvent of water and an amphiprotic solvent other than water, a mixed solvent of water and an aprotic solvent, or an aprotic solvent. Of the above-mentioned solvents, polar solvents are preferably employed as the aprotic solvents in view of good compatibility with water and good solubility of an electrolyte therein. The present inventors have found that the current efficiency in the electrolytic reduction reaction is extremely low when a mixed solvent of water and an amphiprotic solvent other than water is used. The reason for this is not yet fully elucidated. But, one of the reasons for such a low current efficiency is believed to reside in that part of the aldehyde employed forms an acetal or hemi-acetal with the solvent employed. When a mixed solvent of water and an aprotic solvent is used, the selectivity for a 4-butanolide compound based on the aldehyde employed is extremely low. This is believed to be so because the hydroxyl ions which have been produced by the electrolysis of water and are present in a small quantity in the reaction system are activated by the action of the aprotic solvent to cause undesirable side reactions. Therefore, in order that a 4-butanolide compound may be produced by electrolytic reduction in high yield with a high current efficiency in a homogeneous system, the aprotic solvent should be soley used as the solvent for maintaining the homogeneous system and, in addition, trimethylchlorosilane should necessarily be used. However, as mentioned above, even though a relatively high yield of a 4-butanolide compound and a high current efficiency can be achieved in the homogeneous system by the use of an aprotic solvent and trimethylchlorosilane, the preparation of a 4-butanolide compound in a homogeneous system by electrolytic reduction has still many problems, for example, a high cost of solvents to be used, a high cost of trimethylchlorosilane, a large amount of heat required for distilling off the solvent and a poor handleability of trimethylchlorosilane.

The above-mentioned problems can be overcome to some extent by subjecting to electrolytic reduction an acrylic ester and an aldehyde in the form of an aqueous emulsion. However, simple adoption of the aqueous emulsion in the electrolytic reduction method is not sufficient to eliminate all the drawbacks of the conventional method. Particularly, when an aldehyde having a large number of carbon atoms is used as the starting material, the yield of a 4-butanolide compound and current efficiency for the desired 4-butanolide compound are extremely low.

According to the present invention, the electrolytic reduction of a mixture of an acrylic ester and an aldehyde in the form of an aqueous emulsion is carried out in the presence of at least one phase-transfer catalyst, whereby not only high yield of a 4-butanolide compound but also a high current efficienty can be successfully attained. As such a phase-transfer catalyst which may be used in the present invention, there can be mentioned quaternary ammonium salts and quaternary phosphonium salts. The quaternary ammonium salts and quaternary phosphonium salts to be used as the phase-transfer catalyst in the present invention are capable of conducting an electric current when dissolved in water because they are salts. Therefore, in the present invention, it is not necessarily required to additionally employ an organic or inorganic electrolyte. However, with respect to a quaternary salt having a high molecular weight, that is, having a relatively large number of carbon atoms, the solubility of the salt in water is relatively low and the electrical conductivity is also relatively low. Therefore, in the present invention, it is preferred that when such a high molecular weight quaternary salt is employed as a phase-transfer catalyst, it be employed together with a quaternary salt exhibiting a high electrical conductivity, that is, having a relatively small number of carbon atoms, or an inorganic electrolyte.

As mentioned above, in the present invention, the presence of at least one phase-transfer catalyst contributes to high yield of a 4-butanolide compound and a high current efficiency. This will be clearly understood from Table 1 as will be given later. Table 1 shows the influence of an inorganic electrolyte and a phase-transfer catalyst on selectivity for 4-butanolides and by-products, and current efficiency in the electrolytic reduction using an aqueous emulsion system. As is apparent from Table 1, the use of a phase-transfer catalyst exhibits a high selectivity for 4-butanolides and a high current efficiency as compared with the use of an inorganic electrolyte. Particularly, when an aldehyde having a relatively large number of carbon atoms is used as the starting material, the difference in selectivity for 4-butanolides and current efficiency between the use of an inorganic electrolyte and the use of a phase-transfer catalyst is large. Further, the effect of a phase-transfer catalyst on selectivity for 4-butanolides and current efficiency varies depending on the kind of phase-transfer catalyst itself and the kind of aldehyde used. For example, when an aldehyde having a relatively large number of carbon atoms is used, the use of a quaternary ammonium salt having a relatively large number of carbon atoms in the quaternary ammonium ion moiety exhibits a high selectivity for 4-butanolides and a high current efficiency as compared with the use of a quaternary ammonium salt having a relatively small number of carbon atoms in the quaternary ammonium ion moiety. That is, when an aldehyde having a relatively large number of carbon atoms is used, the size of the quaternary ammonium ion moiety has a great effect on selectivity for 4-butanolides and current efficiency. On the other hand, when an aldehyde having a relatively small number of carbon atoms is used, the size of the quaternary ammonium ion moiety has no significant effect on selectivity for 4-butanolides and current efficiency. Illustratively stated, when an aldehyde having a relatively small number of carbon atoms is used the use of a quaternary ammonium salt having a relatively small number of carbon atoms in the quaternary ammonium ion moiety exhibits only a slight increase in current efficiency as compared with the use of a quaternary ammonium salt having a relatively large number of carbon atoms in the quaternary ammonium ion moiety. The term "size of a quaternary ammonium ion moiety" as used herein is represented by the total number of carbon atoms in the substituent groups of a quaternary ammonium salt of the general formula (I):

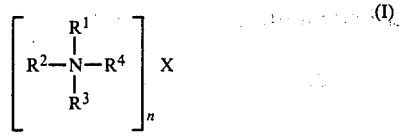

wherein X stands for an acid radical, n stands for an integer corresponding to the valence of X, and $R^1$, $R^2$, $R^3$ and $R^4$ each stand for a substituent group, for example, an alkyl group or an aralkyl group.

In the general formula(I), the total number of carbon atoms in the substituent groups is calculated by the equation n×(carbon number in $R^1$+carbon number in $R^2$+carbon number in $R^3$+carbon number in $R^4$)/n.

The relation between the size of a quaternary ammonium ion moiety and the electrical conductivity and phase-transfer catalytic activity of the quaternary ammonium salt is as follows. The higher the solubility of a quaternary ammonium salt in water, the higher the electrical conductivity of the quaternary ammonium salt. A quaternary ammonium salt having a relatively small size of quaternary ammonium ion moiety exhibits a high solubility in water and, therefore, has a high electrical conductivity when dissolved in water. As such a quaternary ammonium salt exhibiting a high electrical conductivity, there can be mentioned a quaternary ammonium salt having up to 11 carbon atoms in total number of carbon atoms in the substituent groups of a quaternary ammonium salt represented by the general formula(I). However, such a quaternary ammonium salt having a small size of quaternary ammonium ion moiety is relatively poor in phase-transfer catalytic activity. On the other hand, a quaternary ammonium salt having a larger size of quaternary ammonium ion moiety, that is, having at least 12 carbon atoms in total number of carbon atoms in the substituent groups of a quaternary ammonium salt represented by the general formula(I) has a poorer solubility in water and, therefore, exhibits a poorer electrical conductivity, while such a quaternary ammonium salt is relatively excellent in phase-transfer catalytic activity.

Table 2 shows the effect, on selectivity for 4-butanolides and for by-products and current efficiency in the electrolytic reduction using an aqueous emulsion, of an inorganic electrolyte, a mixture of an inorganic electrolyte and a phase-transfer catalyst which is relatively excellent in phase-transfer catalytic activity, and a mixture of a phase-transfer catalyst which is relatively poor in phase-transfer catalytic activity and a phase-transfer catalyst which is relatively excellent in phase-transfer catalytic activity. As is apparent from Table 2, the use of at least one phase-transfer catalyst exhibits a high selectivity for 4-butanolides and a high current efficiency as compared with the sole use of an inorganic electrolyte. Further, when an aldehyde having a relatively large number of carbon atoms is used as the starting material, a combined use of a phase-transfer catalyst which is relatively excellent in phase-transfer catalytic activity, that is, a quaternary phosphonium salt or a quaternary ammonium salt having a relatively large number of carbon atoms and an inorganic or a phase-transfer catalyst which is relatively excellent in electrical conductivity, that is, a quaternary ammonium salt having relatively small number of carbon atoms in the quaternary ammonium ion moiety is very advantageous for improving the selectivity for 4-butanolides and current efficiency.

TABLE 1

| | Aldehyde: butanal (carbon atoms: 4) Acrylic ester: methyl acrylate | | | Aldehyde: heptanal (carbon atoms: 7) Acrylic ester: methyl acrylate | | |
|---|---|---|---|---|---|---|
| Inorganic electrolyte | $KH_2PO_4$ | None | None | $KH_2PO_4$ | None | None |
| Phase-transfer catalyst | None | $[(C_2H_5)_4N]_2SO_4$ | $[(n-C_4H_9)_4N]_2SO_4$ | None | $[(n-C_3H_7)_4N]_2SO_4$ | $[(n-C_4H_9)_4N]_2SO_4$ |
| Current efficiency for a 4-butanolide compound (%) | 40 | 68 | 63 | 4 | 31 | 52 |
| Selectivity for a 4-butanolide compound (%) | | | | | | |
| Based on methyl acrylate | 48 | 77 | 66 | 5 | 37 | 56 |
| Based on aldehyde | 37 | 82 | 90 | 26 | 88 | 91 |
| Selectivity for alcohol | 53 | 13 | 1 | 70 | 10 | 2 |
| Selectivity for methyl propionate | 9 | 5 | 1 | 82 | 17 | 15 |
| Selectivity for dimethyl | 1 | 1 | 8 | 10 | 29 | 28 |

TABLE 1-continued

| | Aldehyde: butanal (carbon atoms: 4) Acrylic ester: methyl acrylate | Aldehyde: heptanal (carbon atoms: 7) Acrylic ester: methyl acrylate |
|---|---|---|
| adipate | | |

TABLE 2

| | Aldehyde: butanal (carbon atoms: 4) Acrylic ester: methyl acrylate | | Aldehyde: heptanal (carbon atoms: 7) Acrylic ester: methyl acrylate | |
|---|---|---|---|---|
| Inorganic electrolyte | $KH_2PO_4$ | $KH_2PO_4$ | $KH_2PO_4$ | $KH_2PO_4$ |
| Phase-transfer catalyst having a relatively small number of carbon atoms | None | None | None | None |
| Phase-transfer catalyst having a relatively large number of carbon atoms | None | $[(n-C_4H_9)_4N]_2SO_4$ | None | $[(n-C_4H_9)_4N]_2SO_4$ |
| Current efficiency for a 4-butanolide compound (%) | 40 | 58 | 4 | 42 |
| Selectivity for a 4-butanolide compound (%) | | | | |
| Based on methyl acrylate | 48 | 70 | 5 | 49 |
| Based on aldehyde | 37 | 58 | 26 | 82 |
| Selectivity for alcohol (%) | 53 | 16 | 70 | 15 |
| Selectivity for methyl propionate (%) | 9 | 1 | 82 | 32 |
| Selectivity for dimethyl adipate (%) | 1 | 2 | 10 | 17 |

| | Aldehyde: heptanal (carbon atoms: 7) Acrylic ester: methyl acrylate | | | |
|---|---|---|---|---|
| Inorganic electrolyte | None | None | None | None |
| Phase-transfer catalyst having a relatively small number of carbon atoms | $[(C_2H_5)_4N]_2SO_4$ | $[(C_2H_5)_4N]_2SO_4$ | $[(C_2H_5)_4N]_2SO_4$ | $[(C_2H_5)_4N]_2SO_4$ |
| Phase-transfer catalyst having a relatively large number of carbon atoms | $(n-C_3H_7)_4NBr$ | $[(n-C_4H_9)_4N]_2SO_4$ | $C_6H_5CH_2N(C_4H_9)_3Cl$ | $(n-C_4H_9)_4PBr$ |
| Current efficiency for a 4-butanolide compound (%) | 22 | 56 | 45 | 58 |
| Selectivity for a 4-butanolide compound (%) | | | | |
| Based on methyl acrylate | 24 | 63 | 50 | 65 |
| Based on aldehyde | 63 | 83 | 90 | 88 |
| Selectivity for alcohol (%) | 30 | 11 | 4 | 6 |
| Selectivity for methyl propionate (%) | 25 | 9 | 7 | 5 |
| Selectivity for dimethyl adipate (%) | 40 | 29 | 25 | 16 |

From the results shown in Table 1, it is presumed that the quaternary ammonium salts listed therein each serve as both an electrolyte and a phase-transfer catalyst. On the other hand, it is presumed from the results shown in Table 2 that the quaternary ammonium salts having a relatively large number of carbon atoms in the substituent groups each serve mainly as a phase-transfer catalyst and the quaternary ammonium salts having a relatively small number of carbon atoms in the substituent groups each serve mainly as an electrolyte.

As described before, when the aldehyde used has a relatively large number of carbon atoms, there may advantageously be employed, as a phase-transfer catalyst, a quaternary ammonium salt having a relatively large number of carbon atoms in the quaternary ammonium ion moiety. In this instance, however, because of a relatively poor electrical conductivity of the above-mentioned quaternary ammonium salt, an inorganic electrolyte or a quaternary ammonium salt having a relatively small number of carbon atoms in the quaternary ammonium ion moiety may preferably be additionally used. However, even when an aldehyde having a relatively large number of carbon atoms is used, a quaternary ammonium salt can be soley used as the phase-transfer catalyst if the kind of the quaternary ammonium salt to be used is properly selected as will be described later. Whilst, when the aldehyde used has a relatively small number of carbon atoms, the sole use of a quaternary ammonium salt having a relatively small number of carbon atoms in the quaternary ammonium ion is sufficient with respect to both phase-transfer catalytic activity and electrical conductivity-imparting property. The use of a quaternary phosphonium salt as a phase-transfer catalyst is sufficient for any aldehyde irrespective of carbon number thereof as far as the phase-transfer catalytic activity is concerned. However, because of a relatively poor electrical conductivity of the quaternary phosphonium salt, there may preferably be additionally employed an inorganic electrolyte or a quaternary ammonium salt having a relatively small number of carbon atoms in the quaternary ammonium ion moiety so that the reaction system is imparted with sufficient electrical conductivity.

The reaction mechanism involved in the process of the present invention will now be explained in connection with the above-mentioned preferred modes of use of an aldehyde, a phase-transfer catalyst and/or an inorganic electrolyte.

The solubility of aldehyde in water varies depending on the kind of aldehyde, particularly the number of carbon atoms of the aldehyde employed. An aldehyde having a relatively small number of carbon atoms, for example, an aldehyde having 1 to 4 carbon atoms dissolves in water well and the solubility thereof in water is comparable favorably with that of methyl acrylate which is a reactant in the process of the present invention. Because of a high solubility of the aldehyde in water, in addition to methyl acrylate, a considerable amount of the aldehyde is present in the water phase of the aqueous emulsion. In such a water phase, it is believed that electrons supplied at the cathode attack the methyl acrylate and the aldehyde present in the water phase to form anions and coupling reaction for the formation of a 4-butanolide compound proceeds to some extent. When, for example, quaternary ammonium ions as the phase-transfer catalyst are present in the water phase, the quaternary ammonium ions form ion pairs with the anions, which prevents the anions from accepting protons. Therefore, the undesirable formation of alcohol and methyl propionate as by-products can be effectively prevented and the coupling reaction for the formation of a 4-butanolide compound is promoted. Further, since the quaternary ammonium ions pull part of the anions into the organic phase as ion pairs, the coupling reaction for the formation of a 4-butanolide compound is further promoted. On the other hand, an aldehyde having a relatively large number of carbon atoms, for example, an aldehyde having at least 5 carbon atoms has a low solubility in water as compared with an aldehyde having up to 4 carbon atoms. Therefore, when an aldehyde having a relatively large number of carbon atoms is employed, the amount of the aldehyde present in the water phase of the aqueous emulsion becomes small. Particularly, when an aldehyde having a greatly large number of carbon atoms is used a little or no amount of aldehyde is present in the water phase. In such a water phase, it is believed that electrons supplied at the cathode attack mainly the acrylic ester to form acrylic ester anions. But, since the aldehyde is present in the water phase only in a small amount, the coupling reaction for the formation of a 4-butanolide compound cannot proceed sufficiently. Therefore, when a phase-transfer catalyst is absent in the water phase, the resulting anions accept protons to form alcohol and methyl propionate and hence the selectivity for a 4-butanolide compound is remarkably lowered. Therefore, in order to suppress the formation of by-products and promote the coupling reaction of the resulting anions with the aldehyde present in a large amount in the organic phase, it is needed to transfer the anions to the organic phase by means of a phase-transfer catalyst. In this case, a phase-transfer catalyst which is excellent in phase-transfer catalytic activity is preferably employed. The reason for this will be described below in connection with quaternary ammonium salts.

When a quaternary ammonium salt having a relatively small number of carbon atoms in the substituent groups of the quaternary ammonium ion moiety is used as the phase-transfer catalyst, the quaternary ammonium ions form ion pairs with the anions, which prevents the anions from accepting protons and suppresses the formation of alcohol and methyl propionate. Part of the resulting ion pairs transfers to the organic phase and the anions are caused to couple with the aldehyde present in the organic phase. Therefore, the selectivity for a 4-butanolide compound is increased to some extent. However, since such a quaternary ammonium salt having a relatively small number of carbon atoms in the substituent groups is relatively poor in phase-transfer catalytic activity, a sufficient amount of anions cannot be transferred into the organic phase, so that the self-coupling reaction of acrylic ester occurs to form an acrylic diester in a considerable amount.

On the other hand, a quaternary ammonium salt having a relatively large number of carbon atoms in the substituent groups of the quaternary ammonium ion moiety can prevent more effectively the anions of acrylic esters from accepting protons. Further, since such a quaternary ammonium salt is excellent in phase-transfer catalytic activity, the anions paired with the quaternary ammonium ions can be effectively transferred into the organic phase. Therefore, in the organic phase, the coupling reaction of the anions with the aldehyde present in the organic phase is extremely promoted.

As is understood from the foregoing, in the process of the present invention, it is preferred that, when a quaternary ammonium salt is soley used as the phase-transfer catalyst, there be used a quaternary ammonium salt which not only conducts sufficiently an electric current when dissolved in water but also exhibits a sufficient phase-transfer catalytic activity. However, when an aliphatic aldehyde having a relatively small number of carbon atoms, for example, an aliphatic aldehyde having up to four carbon atoms is used in the present process, the kind of a quaternary ammonium salt which may be used is not criticl because according to the kind of quaternary ammonium salt, there is no significant difference in selectivity for a 4-butanolide compound and current efficiency for a 4-butanolide compound as shown in Table 1. However, from the standpoint of electrical conductivity, there may be preferably used a quaternary ammonium salt having 4 to 20 carbon atoms, more preferably 4 to 16 carbon atoms in total number of carbon atoms in the substituent groups $R^1$, $R^2$, $R^3$ and $R^4$ in the general formula(I). In such a quaternary ammonium salt, it is preferred that the substituent groups $R^1$, $R^2$, $R^3$ and $R^4$ each be independently an alkyl group or an aralkyl group. Further, it is more preferable that at least one of the substituent groups $R^1$, $R^2$, $R^3$ and $R^4$ be an alkyl group selected from the group consisting of a methyl group, an ethyl group, a propyl group and a butyl group. As such a quaternary ammonium salt, there may be mentioned tetramethylammonium salt, tetraethylammonium salt, tetra-n-propylammonium salt, tetra-iso-propylammonium salt, tetra-n-butylammonium salt, tetra-iso-butylammonium salt, ethyltrimethylammonium salt, diethyldimethylammonium salt, methyltriethylammonium salt, propyltriethylammonium salt, propyltrimethylammonium salt and the like.

When an aldehyde having a relatively large number of carbon atoms, for example, an aliphatic aldehyde having 5 to 13 carbon atoms, an aromatic aldehyde or an aralkyl aldehyde is used as the starting material and a quaternary ammonium salt is soley used as the phase-transfer catalyst, there may be preferably employed a quaternary ammonium salt exhibiting a relatively great phase-transfer catalytic activity but also good electrical conductivity. As such a quaternary ammonium salt, there may be mentioned a quaternary ammonium salt having 12 to 20 carbon atoms in total number of the carbon atoms in the substituent groups $R^1$, $R^2$, $R^3$ and $R^4$ of the quaternary ammonium ion moiety. In such a quaternary ammonium salt, it is preferred that the substituent groups $R^1$, $R^2$, $R^3$ and $R^4$ each be independently an alkyl group or an aralkyl group. Further, it is more preferable that the substituent groups $R^1$, $R^2$, $R^3$ and $R^4$ each be an alkyl group and at least three of them each be an alkyl group having at least three carbon atoms. As such quaternary ammonium salts, there may be mentioned tetra-n-propylammonium salt, tetra-iso-propylammonium salt, tetra-n-butylammonium salt, tetra-iso-butylammonium salt, tetra-n-amylammonium salt, tetra-iso-amylammonium salt, dipropyldibutylammonium salt, ethyltripropylammonium salt, ethyltributylammonium salt, ethylpropyldibutylammonium salt and the like. In the above-mentioned quaternary ammonium salts, it is further preferable that at least one of $R^1$, $R^2$, $R^3$ and $R_4$ be an alkyl group selected from the group consisting of a propyl and a butyl group, and it is most preferable that the alkyl group be a butyl group from the standpoint of availability.

In the present invention, quaternary phosphonium salts can also be solely employed as phase-transfer catalysts. But, as mentioned above, the quaternary phosphonium salts generally exhibit a relatively low electrical conductivity when dissolved in water as compared with the quaternary ammonium salts. Therefore, it is preferred that the quaternary phosphonium salt be employed together with a quaternary ammonium salt exhibiting a good electrical conductivity, namely, a quaternary ammonium salt having a relatively small number of carbon atoms in the quaternary ammonium ion moiety, or an inorganic electrolyte.

When an aldehyde having a relatively large number of carbon atoms, for example, an aliphatic aldehyde having 5 to 13 carbon atoms, an aromatic aldehyde or an aralkyl aldehyde is used as the starting material and a mixture of two or more kinds of quaternary ammonium salts is used as the phasetransfer catalyst, it is preferred that the mixture be selected from those of at least one quaternary ammonium salt which serves mainly as a phasetransfer catalyst and at least one quaternary ammonium salt which serves mainly as an electrolyte.

As described, the quaternary ammonium salts as the phase-transfer catalyst in the process of the present invention are generally classified into two kinds, that is, one is a quaternary ammonium salt exhibiting a high electrical conductivity but relatively low phase-transfer catalytic activity, and the other is a quaternary ammonium salt exhibiting a high phase-transfer catalytic activity but relatively low electrical conductivity.

As the quaternary ammonium salt exhibiting a high electrical conductivity but relatively low phase-transfer catalytic activity there may be mentioned a quaternary ammonium salt having 4 to 11 carbon atoms in total number of carbon atoms in the substituent groups $R^1$, $R^2$, $R^3$ and $R^4$ in the general formula (I). In such a quaternary ammonium salt, each of the substituent groups $R^1$, $R^2$, $R^3$ and $R^4$ is preferably an alkyl group or an aralkyl group, more preferably an alkyl group having up to three carbon atoms. Specific examples of such a quaternary ammonium salt include tetraethylammonium sulfate, tetramethylammonium sulfate, tetraethylammonium-p-toluenesulfonate, tetraethylammonium chloride, methyltriethylammonium chloride and the like. Of the above-mentioned quaternary ammonium salts, a quaternary ammonium salt of the general formula(I) wherein each of the substituent groups $R^1$, $R^2$, $R^3$ and $R^4$ is an ethyl group is most preferred.

On the other hand, as the quaternary ammonium salt exhibiting a high phase-transfer catalytic activity but relatively low electrical conductivity, there may be mentioned a quaternary ammonium salt having 12 to 30 carbon atoms in total number of the carbon atoms in the substituent groups in the general formula(I). In such a quaternary ammonium salt, each of the substituent groups $R^1$, $R^2$, $R^3$ and $R^4$ is preferably an alkyl group or an aralkyl group. Where only one of the substituent groups $R^1$, $R^2$, $R^3$ and $R^4$ has a long chain as compared with the other substituents, the quaternary ammonium salt is surface active and, hence, when it is used, there will be needed a complicated procedure for the separation of a produced 4-butanolide compound from the reaction mixture. It is generally preferred that all the substituent groups $R^1$, $R^2$, $R^3$ and $R^4$ have nearly the same chain lengths.

As preferred examples of the acid radical X of a quaternary ammonium salt represented by the general formula(I), there may be mentioned a sulfate ion, sulfonate ion, phosphate ion, hydrogensulfate ion, hydrogenphosphate ion, dihydrogenphosphate ion or halide ion. Any of the quaternary ammonium salts having the above-mentioned acid radicals exert no adverse effect on the electrode when used in a catalytic amount. However, with respect to quaternary ammonium chlorides, the use thereof in a large amount exerts an adverse effect on the electrode, such as corrosion etc. Therefore, when a quaternary ammonium chloride is employed, it should preferably be employed only in an amount sufficient for providing a phase-transfer catalytic activity in the reaction system while the reaction system is imparted with necessary electrical conductivity by means of other materials as mentioned above. For the reason as mentioned above, in the present invention, a sulfate ion, p-toluenesulfonate ion, hydrogensulfate ion, hydrogenphosphate ion, dihydrogenphosphate ion or phosphate ion may be particularly preferably used as an acid radical X of the quaternary ammonium salt represented by the general formula(I).

When an aldehyde having a relatively large number of carbon atoms, for example, an aliphatic aldehyde having 5 to 13 carbon atoms, an aromatic aldehyde or an aralkyl aldehyde is used as the starting material and a quaternay ammonium salt having a relatively small number of carbon atoms is used together with a quaternary ammonium salt having a relatively large number of carbon atoms or a quaternary phosphonium salt in order to impart to the reaction system a sufficient electrical conductivity rather than a phase-transfer catalytic activity, the amount of such a quaternary ammonium salt having a relatively small number of carbon atoms is not critical unless the electrical resistance of the emulsion comprising a water phase and an organic phase becomes extremely large and the progress of the electrolytic reduction is suppressed. In general, such a quaternary ammonium salt is preferably employed in such an amount that the concentration of the quaternary ammonium salt in the water phase of the emulsion is within the range of 2 to 30% by weight. On the other hand, the amount of a quaternary ammonium salt having a relatively large number of carbon atoms and exhibiting a high phase-transfer catalytic activity which is used together with the above-mentioned quaternary ammonium salt having a relatively small number of carbon atoms or an inorganic electrolyte is preferably 0.1 to 50 mol % based on the amount of the acrylic ester or the aldehyde, whichever is less in amount employed. When there is solely used a quaternary ammonium salt of the kind useful for both the purposes of improving an electrical conductivity and providing a phase-transfer catalytic activity, it is preferred that the quaternary ammonium salt be employed in such an amount that the concentration of the quaternary ammonium salt in the water phase of the emulsion is within the range of 2 to 30% by weight.

As mentioned above, in the process of the present invention, the quaternary phosphonium salts are preferably employed only for the purpose of providing a phase-transfer catalytic activity. Specific examples of the quaternary phosphonium salts include tetra-n-butylphosphonium bromide, triphenylmethylphosphonium iodide, tetraphenylphosphonium chloride and the like. With respect to the amount of the quaternary phosphonium salt to be employed in the process of the present invention, it is preferred that the quaternary phosphonium salt be employed in an amount of 0.1 to 50 mol % based on the amount of the acrylic ester or the aldehyde, whichever is less in amount employed.

In the process of the present invention, phase-transfer catalysts other than quaternary ammonium salts and quaternary phosphonium salts, for example, crown ethers, cryptands and the like may also be employed. In this instance, additional use of an inorganic electrolyte or the like is necessary. But any of these phase transfer-catalysts are not readily available and, in addition, are difficult to recover from the electrolyte after completion of the desired electrolytic reduction as compared with the quaternary ammonium salts and quaternary phosphonium salts.

In the present invention, quaternary ammonium salts are most preferably employed for such a reason that the quaternary ammonium salts are inexpensive as compared with the quaternary phosphonium salts and there is no fear of water pollution and the like.

As inorganic electrolytes which may be employed in the present invention, there can be mentioned at least one inorganic compound selected from the group consisting of sulfuric acid, phosphoric acid, an alkali metal hydrogensulfate, an alkali metal sulfate, a dialkali metal hydrogenphosphate and an alkali metal dihydrogenphosphate. The amount of the inorganic electrolyte to be employed in the present invention is not critical unless the electrical resistance of the emulsion comprising a water phase and an organic phase becomes extremely large and the progress of the electrolytic reduction is suppressed. In general, the inorganic electrolyte is preferably employed in such an amount that the concentration of the inorganic electrolyte in the water phase of the emulsion is within the range of 2 to 30% by weight.

As the cathode to be employed in the present invention, there can be mentioned a lead electrode; a lead alloy electrode made of a lead-based alloy such as a hard lead containing lead and antimony and an alloy of lead and tin; and the like. Unlike a graphite electrode activated by means of mercury, these cathodes not only create no environmental pollution but also have an excellent mechanical strength, so that a long period of stable electrolytic operation can be achieved even when these cathodes are used in a filter press-type electrolytic cell in which multiple electrodes are employed.

The kind of anode employed in the present invention is not critical as far as the anode materials are not attacked by the anolyte. As the material for anode which is generally employed in the present invention, there may be mentioned lead; a lead alloy; platinum; silver; an alloy based on platinum or silver; silver plutinum, a silver alloy or a platinum alloy plated on a metal; and the like.

In the present invention, the electrolytic reduction of a mixture of an acrylic ester and an aldehyde for the preparation of a 4-butanolide compound can be carried out in either a diaphragm-type electrolytic cell (which is a two-compartment electrolytic cell partitioned by a diaphragm) or a diaphragmless electrolytic cell. The disphragmless electrolytic cell has several advantages that the electrolytic voltage is low and the structure of the apparatus is very simple. But, during the electrolytic reduction, oxygen is generated on the surface of the anode and a small amount of hydrogen is generated on the surface of the cathode, so that an explosive gas mixture tends to be produced in the diaphragmless cell. For this reason, in the present invention, it is preferred that a diaphragm-type electrolytic cell partitioned into the cathode compartment and the anode compartment by means of a diaphragm be employed. As a diaphragm which may be used for partitioning the electrolytic cell, there may be mentioned a cation exchange membrane, a membrane made of biscuit and the like. Of the above-mentioned diaphragms, a cation exchange membrane is most preferred because it can pass $H^+$ selectively. Particularly, a cation exchange membrane having a sulfonic acid group as an ion exchange group is preferably employed from the standpoint of chemical and physical stability.

In the present invention, an aqueous solution of an inorganic acid such as sulfuric acid or phosphoric acid is generally employed as the anolyte in the electrolytic cell.

On the other hand, during the electrolytic reduction, the catholyte comprises an acrylic ester, an aldehyde, at least one phase-transfer catalyst, a 4-butanolide compound, by-products such as adipic diester, propionic ester and alcohol, water and, if necessary, an inorganic electrolyte. The above-mentioned catholyte in the present process is an aqueous emulsion comprising two phase, i.e., a water phase and an organic phase. In the present invention, various additives such as a polymerization inhibitor for the acrylic ester and an emulsifying agent for the stabilization of emulsion may be optionally added into the catholyte. Further, an organic solvent may also be optionally added into the catholyte unless the solvent exerts an adverse effect on formation of an emulsion. However, the use of additives such as polymerization inhibitor, emulsifying agent and solvent does occasionally not only has an adverse effect on the electrolytic reduction, for example, an increase in electrolytic voltage but also requires additional steps for separating these additives after completion of the desired electrolytic reduction. Therefore, usually, the electrolytic reduction is preferably carried out in the absence of these additives.

As the acrylic ester to be employed as the starting material in the process of the present invention, a lower alkyl ester of acrylic acid is preferably employed from the standpoint of solubility in water, availability and cost. Particularly, methyl acrylate is most preferred.

As preferred examples of the aldehyde to be employed in the process of the present invention, there may be mentioned an aliphatic aldehyde, an aromatic aldehyde and an aralkyl aldehyde. Of the above-mentioned aldehydes, there may be more preferably employed an aliphatic aldehyde having up to 13 carbon atoms. Specific examples of such an aliphatic aldehyde, there may be mentioned, for example, propanal, butanal, methylpropanal, heptanal, methylhexanal, hexanal, methylpentanal, methylheptanal, octanal, methyloctanal and nonanal.

In the process of the present invention, the molar ratio of an aldehyde to an acrylic ester is preferably 1 to 10 from a standpoint of yield of a desired 4-butanolide compound, more preferably 1 to 5 from a further standpoint of ease in separation of a desired 4-butanolide compound.

The total amount of an aldehyde and an acrylic ester relative to water is more than that corresponding to the solubility of the aldehyde and acrylic ester in water so that an aqueous emulsion comprising an organic phase and a water phase can be formed. The organic phase is preferably present in the aqueous emulsion in a volume ratio of 0.05 to 0.5 relative to the total volume of the aqueous emulsion.

The temperature of the electrolytic reduction in the present process is not critical as far as neither an aldehyde nor an acrylic ester will boil. However, in general, the electrolytic reduction is preferably carried out at 20° to 60° C., more preferably 20° to 40° C. from the standpoint of prevention of heat denaturation of the aldehyde and acrylic ester.

In the present invention, the current density on the surface of the cathode is preferably 1 to 50 A/dm$^2$. When the current density is less than 1 A/dm2, the productivity of a desired 4-butanolide compound is lowered, so that an electrode having a wide area should be used. On the other hand, when the current density is more than 50 A/dm$^2$, an unfavorably remarkable generation of heat due to a liquid resistance occurs. Therefore, it is preferred that the current density on the surface of the cathode is within the above-mentioned range, more preferably 5 to 20 A/dm$^2$.

The water phase and organic phase constituting the aqueous emulsion are preferably contacted with the surface of the cathode in the form of fine liquid particles as much as possible. Therefore, when an electrolytic cell for a batchwise production is used, it is necessary to mix sufficiently the electrolyte by agitation. On the other hand, when a filter press-type electrolytic cell is used, it is preferred that the catholyte be supplied into the cell at such a linear velocity as will form an aqueous emulsion during the supply, that is, at a linear velocity of 100 to 400 cm/sec.

In practicing the process of the present invention, the catholyte which has been subjected to electrolysis is usually treated as follows.

The catholyte is allowed to stand so that it is separated into two phases, namely, an organic phase and a water phase. The phase-transfer catalyst distributed in the organic phase is extracted with a small amount of water and, then, the organic phase is subjected to distillation. In the distillation, by-products having a low boiling point such as methanol are first removed, unreacted starting materials are secondly recovered and, finally, the intended product is obtained. With respect to the water phase, it is also subjected to distillation, so that by-products having a low boiling point such as methanol are first distilled off and, then, water is removed in an amount corresponding to the amount of water which transferred from the anode chamber to the cathode chamber through a cation exchange membrane. The residual liquid containing the phase-transfer catalyst and the inorganic electrolyte, if any, is reused as a water source for a fresh catholyte.

According to the present invention, the separation of the intended products and the recovery of the phase-transfer catalyst and the inorganic electrolyte can be easily performed by the above-mentioned procedures.

The advantages of the process of the present invention are summarized as follows:

(1) A 4-butanolide compound can be prepared with a high current efficiency and selectivity without using expensive agents, such as dimethylforamide and trimethylchlorosilane, by subjecting an aqueous emulsion containing an acrylic ester and an aldehyde to electrolytic reduction in the presence of at least one phase-transfer catalyst. Further, an adipic diester which is produced as a by-product can be advantageously utilized as a useful raw material in the field of chemical industry.

(2) Since a cathode used in the present invention is made of lead or a lead alloy composed mainly of lead which not only creates no pollution problem but also has an excellent mechanical strength, the process of the present invention is quite advantageous from a commercial point of view.

(3) The separation of the intended products can be performed with great ease. The electrolyzed catholyte in the form of an aqueous emulsion from the electrolytic cell after electrolysis can be easily separated into an organic phase composed mainly of an acrylic ester, an aldehyde and a desired 4-butanolide compound, and a water phase composed mainly of water and inorganic electrolyte, for example, by allowing the catholyte to stand. Also, the intended product can be easily isolated and purified by subjecting the separated organic phase to distillation. In the distillation, it is not necessary to recover a large quantity of solvent as opposed to the production of the desired 4-butanolide compound by electrolysis of a homogeneous solution. Therefore a remarkable reduction of working cost can be achieved. The separated water phase can be reused as a water source for a fresh catholyte after simple treatments.

(4) The phase-transfer catalyst dissolved in the organic phase containing a desired 4-butanolide compound can be easily recovered. As mentioned in (3) above, the organic phase can be easily separated from the water phase and then the phase-transfer catalyst dissolved in the organic phase can be easily recovered by extraction with water.

(5) Since any peroxide compound is not employed in the process of the present invention, the reaction can be conducted under mild conditions without danger.

As apparent from the above, the process of the present invention is very advantageous for the preparation of a 4-butanolide compound from an acrylic ester and an aldehyde from a practical point of view.

The present invention will now be described in more detail with reference to the following Examples that should not be construed as limiting the scope of the invention.

Herein, assuming that two faradays of electricity produce one mole of a 4-butanolide compound, current efficiency was determined according to the following equation:

Current efficiency [%] =

$$\frac{\text{(mole number of produced 4-butanolide)} \times 2}{\text{current quantity [faraday]}} \times 100$$

The proportion of the current quantity having passed through a reaction system relative to the theoretical quantity of electricity that is a quantity of electricity theoretically required for completion of the reaction is hereinafter often referred to simply as "relative current quantity" and is given by the following equation:

Relative current quantity [%] =

$$\frac{\text{current quantity having passed through a reaction system [faraday]}}{\text{(mole number of charged acrylic ester)} \times 2} \times 100$$

Conversion of starting materials and selectivities for a 4-butanolide compound and by-products are defined as follows.

Conversion of acrylic ester [%] =

$$\frac{\text{mole number of consumed acrylic ester}}{\text{mole number of charged acrylic ester}} \times 100$$

Conversion of aldehyde [%] =

$$\frac{\text{mole number of consumed aldehyde}}{\text{mole number of charged aldehyde}} \times 100$$

Selectivity for 4-butanolide based on acrylic ester [%] =

$$\frac{\text{mole number of produced 4-butanolide}}{\text{mole number of consumed acrylic ester}} \times 100$$

Selectivity for 4-butanolide based on aldehyde [%] =

$$\frac{\text{mole number of produced 4-butanolide}}{\text{mole number of consumed aldehyde}} \times 100$$

Selectivity for primary alcohol as a by-product formed by reduction of aldehyde [%] =

$$\frac{\text{mole number of produced primary alcohol}}{\text{mole number of consumed aldehyde}} \times 100$$

Selectivity for propionic ester as a by-product [%] =

$$\frac{\text{mole number of produced propionic ester}}{\text{mole number of consumed acrylic ester}} \times 100$$

Selectivity for adipic diester as a by-product [%] =

$$\frac{\text{(mole number of produced adipic diester)} \times 2}{\text{mole number of consumed acrylic ester}} \times 100$$

EXAMPLE 1

As an electrolytic cell, there was used an H-shaped electrolytic cell comprising an anode chamber and a cathode chamber communicating with said anode chamber through a 1.6 mm-thick cation exchange membrane of sulfonated divinylbenzene-styrene-butadiene copolymer disposed between the anode and cathode chambers. The H-shaped electrolytic cell was provided with an anode plate made of lead in the anode chamber and a cathode plate made of lead in the cathode chamber, each plate having a current-flowing area of 0.0431 dm$^2$. 10 wt% sulfuric acid was used as an anolyte. As a catholyte was used a mixture of 5.37 g (74.6 mmol) of butanal, 2.17 g (25.2 mmol) of methyl acrylate, 54.9 g of water and 6.23 g (17.5 mmol) of tetraethylammonium sulfate. The electrolysis was carried out at a catholyte temperature of 27° to 28° C. and a current density of 10.2 A/dm$^2$ while sufficiently stirring the catholyte by means of a magnetic stirrer. The electrolysis was discontinued when the relative current quantity reached 106%. Then, the catholyte was analyzed by gas chromatography. The results are as follows:

conversion of methyl acrylate, 94%; conversion of butanal, 30%; selectivity for 4-n-propyl-4-butanolide based on acrylic ester, 77%; selectivity for 4-n-propyl-4-butanolide based on butanal, 82%; current efficiency, 68%; selectivity for 1-butanol, 13%; selectivity of methyl propionate, 5%; and selectivity for dimethyl adipate, 1%.

EXAMPLE 2

In substantially the same manner as in Example 1, the electrolysis was carried out except that 9.88 g (17.0 mmol) of tetra-n-butylammonium sulfate was used instead of 6.23 g (17.5 mmol) of tetraethylammonium sulfate. After the electrolysis, the catholyte was analyzed in the same manner as in Example 1. The results are as follows:

conversion of methyl acrylate, 100%; conversion of butanal, 25%; selectivity for 4-n-propyl-4-butanolide based on methyl acrylate, 66%; selectivity for 4-n-propyl-4-butanolide based on butanal, 90%; current efficiency, 63%; selectivity for 1-butanol, 1%; selectivity for methyl propionate, less than 1%; and selectivity for dimethyl adipate, 8%.

EXAMPLE 3

The electrolytic cell as described in Example 1 and 10 wt% sulfuric acid as an anolyte were used. As a catholyte was used a mixture of 5.41 g (75.1 mmol) of butanal, 2.17 g (25.2 mmol) of methyl acrylate, 54.8 g of water and 4.23 g (17.3 mmol) of tetramethylammonium sulfate. The electrolysis was carried out at a catholyte temperature of 28° to 30° C. and a current density of 10.2 A/dm$^2$ while sufficiently stirring the catholyte by means of a magnetic stirrer. The electrolysis was discontinued when the relative current quantity reached 105%. Then, the catholyte was analyzed in the same manner as in Example 1. The results are as follows:

conversion of methyl acrylate, 95%; conversion of butanal, 31%; selectivity for 4-n-propyl-4-butanolide based on acrylic ester, 73%; selectivity for 4-n-propyl-4-butanolide based on butanal, 76%, current efficiency, 66%; selectivity for 1-butanol, 20%, selectivity for methyl propionate, 5%; and selectivity for dimethyl adipate, 1%.

EXAMPLE 4

In substantially the same manner as in Example 1, the electrolysis was carried out except that 8.10 g (22.7 mmol) of tetra-n-propylammonium-p-toluenesulfonate was used instead of 6.23 g (17.5 mmol) of tetraethylammonium sulfate. After the electrolysis, the catholyte was analyzed in the same manner as in Example 1. The results are as follows:

conversion of methyl acrylate, 100%; conversion of butanal, 27%; selectivity for 4-n-propyl-4-butanolide based on acrylic ester, 72%; selectivity for 4-n-propyl-4-butanolide based on butanal, 89%; current efficiency, 68%; selectivity for 1-butanol, 8%; selectivity for methyl propionate, 5%; and selectivity for dimethyl adipate, 6%.

EXAMPLE 5

In substantially the same manner as in Example 1, the electrolysis was carried out except that 10.41 g (34.6 mmol) of tetraethylammonium-p-toluenesulfonate was used instead of 6.23 g of tetraethylammonium sulfate and that the catholyte temperature was maintained at 46° to 47° C. instead of 27° to 28° C. After the electrolysis, the catholyte was analyzed in the same manner as in Example 1. The results are as follows:

conversion of methyl acrylate, 88%; conversion of butanal, 34%; selectivity for 4-n-propyl-4-butanolide based on methyl acrylate, 60%; selectivity for 4-n-propyl-4-butanolide based on butanal, 52%; and current efficiency, 50%.

EXAMPLE 6

The electrolytic cell as described in Example 1 and 10% sulfuric acid as an anolyte were used. As a catholyte was used a mixture of 13.11 g (226 mmol) of propanal, 6.41 g (74.5 mmol) of methyl acrylate, 52.1 g of water and 4.23 g (17.3 mmol) of tetramethylammonium sulfate. The electrolysis was carried out at a catholyte temperature of 28° to 31° C. and a current density of 10.2 A/dm$^2$ while sufficiently stirring the catholyte by means of a magnetic stirrer. The electrolysis was discontinued when the relative current quantity reached 103%. Then, the catholyte was analyzed in the same manner as in Example 1. The results are as follows:

conversion of methyl acrylate, 85%; conversion of propanal, 30%; selectivity for 4-ethyl-4-butanolide based on methyl acrylate, 80% selectivity for 4-ethyl-4-butanolide based on propanal, 75%; and current efficiency, 66%.

EXAMPLE 7

The electrolytic cell as described in Example 1 and 10 wt% sulfuric acid as an anolyte were used. As a catholyte was used a mixture of 8.71 g (76.4 mmol) of heptanal, 2.18 g (25.4 mmol) of methyl acrylate, 57.6 g of water and 9.99 g (17.2 mmol) of tetra-n-butylammonium sulfate. The electrolysis was carried out at a catholyte temperature of 28° to 29° C. and a current density of 10.2 A/dm$^2$ while sufficiently stirring the catholyte by means of a magnetic stirrer. The electrolysis was discontinued when the relative current quantity reached 105%. Then, the catholyte was analyzed in the same manner as in Example 1. The results are as follows:

conversion of methyl acrylate, 97%; conversion of heptanal, 20%; selectivity for 4-n-hexyl-4-butanolide based on methyl acrylate, 56%; selectivity for 4-n-hexyl-4-butanolide based on heptanal, 91%; current efficiency, 52%; selectivity for 1-heptanol, 2%; selectivity for methyl propionate, not more than 15%; and selectivity for dimethyl adipate, 28%.

EXAMPLE 8

The electrolytic cell as described in Example 1 and 10 wt% sulfuric acid as an anolyte were used. As a catholyte was used a mixture of 8.59 g (75.4 mmol) of heptanal, 2.16 g (25.1 mmol) of methyl acrylate, 51.6 g of water and 8.11 g (17.3 mmol) of tetra-n-propylammonium sulfate. The electrolysis was carried out at a catholyte temperature of 28° to 29° C. and a current density of 10.2 A/dm$^2$ while sufficiently stirring the catholyte by means of a magnetic stirrer. The electrolysis was discontinued when the relative current quantity reached 104%. Then, the catholyte was analyzed in the same manner as in Example 1. The results are as follows:

conversion of methyl acrylate, 86%; conversion of heptanal, 12%; selectivity for 4-n-hexyl-4-butanolide based on methyl acrylate, 37%; selectivity for 4-n-hexyl-4-butanolide based on heptanal, 88%; current efficiency, 31%; selectivity for 1-heptanol, 10%; selectivity for methyl propionate, 17%; and selectivity for dimethyl adipate, 29%.

EXAMPLE 9

In substantially the same manner as in Example 1, the electrolysis was carried out except that a mixture of 9.64 g (75.3 mmol) of octanal, 2.16 g (25.1 mmol) of methyl acrylate, 52.1 g of water and 10.0 g (17.2 mmol) of tetra-n-butylammonium sulfate was used as an catholyte instead of the catholyte as used in Example 1. After the electrolysis, the catholyte was analyzed in the same manner as in Example 1. The results are as follows:

conversion of methyl acrylate, 83%; conversion of octanal, 18%; selectivity for 4-n-heptyl-4-butanolide based on methyl acrylate, 50%; selectivity for 4-n-heptyl-4-butanolide based on octanal, 77%; and current efficiency, 40%.

EXAMPLE 10

The electrolytic cell as described in Example 1 and 10 wt% sulfuric acid as an anolyte were used. As a catholyte was used a mixture of 5.28 g (73.3 mmol) of butanal, 2.17 g (25.2 mmol) of methyl acrylate, 55.1 g of water, 2.36 g of potassium dihydrogenphosphate as inorganic electrolyte and 0.107 g (0.184 mmol) of tetra-n-butylammonium bromide. The electrolysis was carried out at a catholyte temperature of 26° to 29° C. and a current density of 10.2 A/dm$^2$ while sufficiently stirring the catholyte by means of a magnetic stirrer. The electrolysis was discontinued when the relative current quantity reached 103%. Then, the catholyte was analyzed in the same manner as in Example 1. The results are as follows:

conversion of methyl acrylate, 87%; conversion of butanal, 36%; selectivity for 4-n-propyl-4-butanolide based on methyl acrylate, 74%; selectivity for 4-n-propyl-4-butanolide based on butanal, 61%; current efficiency, 63%; selectivity for 1-butanol, 16%; selectivity for methyl propionate, less than, 1%; and selectivity for dimethyl adipate, 2%.

EXAMPLE 11

The electrolytic cell as described in Example 1 and 10 wt% sulfuric acid as an anolyte were used. As a catholyte was used a mixture of 5.24 g (72.8 mmol) of butanal, 2.13 g (24.8 mmol) of methyl acrylate, 54.6 g of water, 2.36 g of potassium dihydrogenphosphate as an inorganic electrolyte and 0.193 g (0.333 mmol) of tetra-n-butylammonium sulfate. The electrolysis was carried out at a catholyte temperature of 28° to 33° C. and a current density of 10.2 A/dm$^2$ while sufficiently stirring the catholyte by means of a magnetic stirrer. The electrolysis was discontinued when the relative current quantity reached 107%. Then, the catholyte was analyzed in the same manner as in Example 1. The results are as follows:

conversion of methyl acrylate, 89%; conversion of butanal, 37%; selectivity for 4-n-propyl-4-butanolide based on methyl acrylate, 70%; selectivity for 4-n-propyl-4-butanolide based on butanal, 58%; current efficiency, 58%; selectivity for 1-butanol, 16%; selectivity for methyl propionate, less than 1%; and selectivity for dimethyl adipate, 3%.

EXAMPLE 12

The electrolytic cell as described in Example 1 and 10 wt% sulfuric acid as an anolyte were used. As a catholyte was used a mixture of 5.27 g (73.2 mmol) of butanal, 2.12 g (24.7 mmol) of methyl acrylate, 54.8 g of water, 2.36 g of potassium dihydrogenphosphate as an inorganic electrolyte and 0.195 g (0.336 mmol) of tetra-n-butylammonium sulfate. The electrolysis was carried out at a catholyte temperature of 46° to 47° C. and a current density of 10.2 A/dm$^2$ while sufficiently stirring the catholyte by means of a magnetic stirrer. The electrolysis was discontinued when the relative current quantity reached 103%. Then, the catholyte was analyzed in the same manner as in Example 1. The results are as follows:

conversion of methyl acrylate, 93%; conversion of butanal, 40%; selectivity for 4-n-propyl-4-butanolide based on methyl acrylate, 57%; selectivity for 4-n-propyl-4-butanolide based on butanal, 44% current efficiency, 52%; selectivity for 1-butanol, 6%; and selectivity for methyl propionate, 3%.

EXAMPLE 13

The electrolytic cell as described in Example 1 and 10 wt% sulfuric acid as an anolyte were used. As a catholyte was used a mixture of 3.62 g (50.3 mmol) of butanal, 4.34 g (50.5 mmol) of methyl acrylate, 54.0 g of water, 2.38 g of potassium dihydrogenphosphate as an inorganic electrolyte and 0.195 g (0.336 mmol) of tetra-n-butylammonium bromide. The electrolysis was carried out at a catholyte temperature of 27° to 29° C. and a current density of 10.2 A/dm$^2$ while sufficiently stirring the catholyte by means of a magnetic stirrer. The electrolysis was discontinued when the relative current quantity reached 51%. Then, the catholyte was analyzed in the same manner as in Example 1. The results are as follows:

conversion of methyl acrylate, 63%; conversion of butanal, 41%; selectivity for 4-n-propyl-4-butanolide based on methyl acrylate, 43%; selectivity for 4-n-propyl-4-butanolide based on butanal, 68%; current efficiency, 53%; selectivity for 1-butanol, 3%; selectivity for methyl propionate, 4%; and selectivity for dimethyl adipate, 1%.

EXAMPLE 14

The electrolytic cell as described in Example 1 and 10 wt% sulfuric acid as an anolyte were used. As a catholyte was used a mixture of 13.15 g (226 mmol) of propanal, 6.43 g (74.8 mmol) of methyl acrylate, 52.1 g of water, 2.37 g of potassium dihydrogenphosphate as an inorganic electrolyte and 0.193 g (0.333 mmol) of tetra-n-butylammonium sulfate. The electrolysis was carried out at a catholyte temperature of 28° to 30° C. and a current density of 10.2 A/dm$^2$ while sufficiently stirring the catholyte by means of a magnetic stirrer. The electrolysis was discontinued when the relative current quantity reached 114%. Then, the catholyte was analyzed in the same manner as in Example 1. The results are as follows:

conversion of methyl acrylate, 90%; conversion of propanal, 39%; selectivity for 4-ethyl-4-butanolide based on methyl acrylate, 70%; selectivity for 4-ethyl-4-butanolide based on propanal, 53%; current efficiency, 55%; selectivity for 1-propanol, 17%; selectivity for methyl propionate, less than 1%; and selectivity for dimethyl adipate, 1%.

EXAMPLE 15

The electrolytic cell as described in Example 1 and 10 wt% sulfuric acid as an anolyte were used. As a catholyte was used a mixture of 8.61 g (75.5 mmol) of heptanal, 2.20 g (25.6 mmol) of methyl acrylate, 52.0 g of water, 6.23 g of tetraethylammonium sulfate and 1.00 g (1.72 mmol) of tetra-n-butylammonium sulfate. The electrolysis was carried out at a catholyte temperature of 28° to 29° C. and current density of 10.2 A/dm$^2$ while sufficiently stirring the catholyte by means of a magnetic stirrer. The electrolysis was discontinued when the relative current quantity reached 105%. Then, the catholyte was analyzed in the same manner as in Example 1. The results are as follows:

conversion of methyl acrylate, 93%; conversion of heptanal, 24%; selectivity for 4-n-hexyl-4-butanolide based on methyl acrylate, 63%; selectivity for 4-n-hexyl-4-butanolide based on heptanal, 83%; current efficiency, 56%; selectivity for 1-heptanol, 11%; selectivity for methyl propionate, 9%; and selectivity for dimethyl adipate, 28%.

EXAMPLE 16

The electrolytic cell as described in Example 1 and 10 wt% sulfuric acid as an anolyte were used. As a catholyte was used a mixture of 8.61 g (75.5 mmol) of heptanal, 2.18 g (25.4 mmol) of methyl acrylate, 54.2 g of water, 2.39 g of potassium dihydrogenphosphate as an inorganic electrolyte and 1.01 g (1.74 mmol) of tetra-n-butylammonium sulfate. The electrolysis was carried out at a catholyte temperature of 28° to 30° C. and a current density of 10.2 A/dm$^2$ while sufficiently stirring the catholyte by means of a magnetic stirrer. The electrolysis was discontinued when the relative current quantity reached 106%. Then, the catholyte was analyzed in the same manner as in Example 1. The results are as follows:

conversion of methyl acrylate, 90%; conversion of heptanal, 18%; selectivity for 4-n-hexyl-4-butanolide based on methyl acrylate, 49%; selectivity for 4-n-hexyl-4-butanolide based on heptanal, 82%; current efficiency, 42%; selectivity for 1-heptanol, 15%; selectivity for methyl propionate, 32%; and selectivity for dimethyl adipate, 17%.

EXAMPLE 17

In substantially the same manner as in Example 15, the electrolysis was carried out except that 0.94 g (3.53 mmol) of tetra-n-propylammonium bromide was used instead of 1.00 g of tetra-n-butylammonium sulfate. After the electrolysis, the catholyte was analyzed in the same manner as in Example 1. The results are as follows:

conversion of methyl acrylate, 96%; conversion of heptanal, 12%; selectivity for 4-n-hexyl-4-butanolide based on methyl acrylate, 24%; selectivity for 4-n-hexyl-4-butanolide based on heptanal, 63%; current efficiency, 22%; selectivity for 1-heptanol, 30%; selectivity for methyl propionate, 25%; and selectivity for dimethyl adipate, 40%.

EXAMPLE 18

In substantially the same manner as in Example 15, the electrolysis was carried out except that 2.73 g (8.76 mmol) of benzyltri-n-butylammonium chloride was used instead of 1.00 g of tetra-n-butylammonium sulfate. After the electrolysis, the catholyte was analyzed in the same manner as in Example 1. The results are as follows:
conversion of methyl acrylate, 94%; conversion of heptanal, 18%; selectivity for 4-n-hexyl-4-butanolide based on methyl acrylate, 50%; selectivity for 4-n-hexyl-4-butanolide based on heptanal, 90%; current efficiency, 45%; selectivity for 1-heptanol, 4%; selectivity for methyl propionate, 7%; and selectivity for dimethyl adipate, 25%.

EXAMPLE 19

In substantially the same manner as in Example 15, the electrolysis was carried out except that 1.19 g (3.51 mmol) of tetra-n-butylphosphonium bromide was used instead of 1.00 g of tetra-n-butylammonium sulfate. After the electrolysis, the catholyte was analyzed in the same manner as in Example 1. The results are as follows:
conversion of methyl acrylate, 94%; conversion of heptanal, 23%; selectivity for 4-n-hexyl-4-butanolide based on methyl acrylate, 65%; selectivity for 4-n-hexyl-4-butanolide based on heptanal, 88%; current efficiency, 58%; selectivity for 1-heptanol, 6%; selectivity for methyl propionate, 5%; and selectivity for dimethyl adipate, 16%.

EXAMPLE 20

In substantially the same manner as in Example 15, the electrolysis was carried out except that 1.57 g (3.90 mmol) of tri-n-coctylmethylammonium chloride was used instead of 1.00 g of tetra-n-butylammonium sulfate. After the electrolysis, the catholyte was analyzed in the same manner as in Example 1. The results are as follows:
conversion of methyl acrylate, 96%; conversion of heptanal, 18%; selectivity for 4-n-hexyl-4-butanolide based on methyl acrylate, 46%; selectivity for 4-n-hexyl-4-butanolide based on heptanal, 82%; current efficiency, 42%; selectivity for 1-heptanol, 10%; selectivity for methyl propionate, 18%; and selectivity for dimethyl adipate, 32%.

EXAMPLE 21

In substantially the same manner as in Example 15, the electrolysis was carried out except that 1.29 g (3.41 mmol) of cetylethyldimethylammonium bromide was used instead of 1.00 g of tetra-n-butylammonium sulfate. After the electrolysis, the catholyte was analyzed in the same manner as in Example 1. The results are as follows:
conversion of methyl acrylate, 81%; conversion of heptanal, 21%; selectivity for 4-n-hexyl-4-butanolide based on methyl acrylate, 56%; selectivity for 4-n-hexyl-4-butanolide based on heptanal, 74%; current efficiency, 43%; selectivity for 1-heptanol, 19%; selectivity for methyl propionate, 19%; and selectivity for dimethyl adipate, 15%.

EXAMPLE 22

The electrolytic cell as described in Example 1 and 10 wt% sulfuric acid as an anolyte were used. As a catholyte was used a mixture of 8.62 g (75.6 mmol) of heptanal, 2.17 g (25.2 mmol) of methyl acrylate, 45.5 g of water, 10.42 g of tetraethylammonium-p-toluenesulfonate and 1.43 g (3.46 mmol) of tetra-n-butylammonium-p-toluenesulfonate. The electrolysis was carried out at a catholyte temperature of 29° to 30° C. and a current density of 10.2 A/dm$^2$ while sufficiently stirring the catholyte by means of a magnetic stirrer. The electrolysis was discontinued when the relative current quantity reached 105%. Then, the catholyte was analyzed in the same manner as in Example 1. The results are as follows:
conversion of methyl acrylate, 86%; conversion of heptanal, 18%; selectivity for 4-n-hexyl-4-butanolide based on methyl acrylate, 44%; selectivity for 4-n-hexyl-4-butanolide based on heptanal, 70%; and current efficiency, 36%.

EXAMPLE 23

The electrolytic cell as described in Example 1 and 10 wt% sulfuric acid as an anolyte were used. As a catholyte was used a mixture of 9.60 g (75.0 mmol) of octanal, 2.17 g (25.2 mmol) of methyl acrylate, 51.0 g of water, 6.18 g (17.4 mmol) of tetraethylammonium sulfate and 1.02 g (1.76 mmol) of tetra-n-butylammonium sulfate. The electrolysis was carried out at a catholyte temperature of 27° to 30° C. and a current density of 10.2 A/dm$^2$ while sufficiently stirring the catholyte by means of a magnetic stirrer. The electrolysis was discontinued when the relative current quantity reached 105%. Then, the catholyte was analyzed in the same manner as in Example 1. The results are as follows:
conversion of methyl acrylate, 99%; conversion of octanal, 23%; selectivity for 4-n-heptyl-4-butanolide based on methyl acrylate, 57%; selectivity for 4-n-heptyl-4-butanolide based on octanal, 82%; and current efficiency, 54%.

EXAMPLE 24

As an electrolytic cell, there was used a circulation type electrolytic apparatus which was partitioned into an anode chamber and a cathode chamber by a 1.6 mm-thick cation exchange membrane of sulfonated divinylbenzene-styrenebutadiene copolymer. In the anode and cathode chambers were respectively accomodated an anode plate and a cathode plate, each plate being made of lead and having a current-flowing area of 0.58 dm$^2$. The circulation type electrolytic apparatus was designed to circulate an anolyte between an anolyte tank and the anode chamber and to circulate a catholyte between a catholyte tank and the cathode chamber. Each of the anode and cathode plates was spaced apart from the cation exchange membrane by means of a polyethylene-made spacer so that a 2 mm spacing was provided between each electrode and the membrane. 10 wt% sulfuric acid was used as an anolyte. As a catholyte was used a mixture of 46.8 g (0.650 mol) of butanal, 19.2 g (0.223 mol) of methyl acrylate, 456 g of water and 78.0 g (0.219 mol) of tetraethylammonium sulfate. The electrolysis was carried out at a catholyte temperature of 28° to 30° C. and a current density of 10.0 A/dm$^2$ while stirring the catholyte in the electrolytic apparatus by circulating the catholyte at a flow rate of 200 cm/sec between the cathode chamber and the catholyte tank. A mixture of 34.6 g (0.481 mol) of butanal and 36.7 g (0.427 mol) of methyl acrylate was fed into the catholyte tank little by little over five hours during the electrolysis. Even after completion of the feeding of the mixture, the electrolysis was further continued. When the relative current density reached 118%, the electrolysis was stopped. During the electrolysis, the voltage fluctuated between 5.4 V and 5.6 V. After the electrolysis, the catholyte was taken out and allowed to stand so that the catholyte was separated into an organic phase and a water phase. Both the organic and water phases were analyzed by gas chromatography. The results are as follows:

conversion of methyl acrylate, 99%; conversion of butanal, 76%; selectivity for 4-n-propyl-4-butanolide based on methyl acrylate, 85%; selectivity for 4-n-propyl-5-butanolide based on butanal, 63%; current efficiency, 71%; and dimethyl adipate, less than 1%.

EXAMPLE 25

The circulation type electrolytic apparatus as described in Example 24 and 10 wt% sulfuric acid as an anolyte were used. As a catholyte was used a mixture of 73.9 g (0.648 mol) of heptanal, 18.6 g (0.216 mol) of methyl acrylate, 418 g of water, 53 g (0.149 mol) of tetraethylammonium sulfate and 36 g (0.062 mol) of tetra-n-butylammonium sulfate. The electrolysis was carried out at a catholyte temperature of 27° to 29° C. and a current density of 10.0 A/dm$^2$ while stirring the catholyte in the electrolytic apparatus by circulating the catholyte at a flow rate of 200 cm/sec between the cathode chamber and the catholyte tank. A mixture of 45.9 g (0.403 mol) of heptanal and 48.8 g (0.567 mol) of methyl acrylate was fed into the catholyte tank little by little over five hours during the electrolysis. When the relative current quantity reached 66%, the electrolysis was stopped. During the electrolysis, the voltage fluctuated between 5.8 V and 5.9 V. After the electrolysis, the catholyte was allowed to stand so as to be separated into an organic phase and a water phase. The organic phase was washed with 50 g of water and, then, distilled. 10 g of methyl acrylate was recovered from the organic and water phases. 66 g of heptanal was recovered from the organic phase. By distilling the organic phase, 22 g of dimethyl adipate as a by-product and 57 g of 4-n-hexyl-4-butanolide were obtained. The results are summarized as follows:

conversion of methyl acrylate, 85%; conversion of heptanal, 45%; selectivity for 4-n-hexyl-4-butanolide based on methyl acrylate, 50%; selectivity for 4-n-hexyl-4-butanolide based on heptanal, 70%; current efficiency, 65%; and selectivity for dimethyl adipate, 39%.

EXAMPLE 26

In substantially the same manner as in Example 16, the electrolysis was carried out except that 1.19 g (3.51 mmol) of tetra-n-butylphosphonium bromide was used instead of 1.01 g of tetra-n-butylammonium sulfate. After the electrolysis, the catholyte was analyzed in the same manner as in Example 1. The results are as follows:

conversion of methyl acrylate, 91%; conversion of heptanal, 19%; selectivity for 4-n-hexyl-4-butanolide based on methyl acrylate, 51%, selectivity for 4-n-hexyl-4-butanolide based on heptanal, 83% and current efficiency, 44%.

COMPARATIVE EXAMPLE 1

The electrolytic cell as described in Example 1 and 10 wt% sulfuric acid as an anolyte were used. As a catholyte was used a mixture of 1.76 g (15.5 mmol) of heptanal, 0.454 g (5.28 mmol) of methyl acrylate, 18.5 g of water, 6.19 g (17.4 mmol) of tetraethylammonium sulfate and 52.0 g of methanol as a solvent for forming a homogeneous system. The electrolysis was carried out in homogeneous system at a catholyte temperature of 28° to 29° C. and a current density of 10.2 A/dm$^2$. When the relative current quantity reached 122%, the electrolysis was stopped and the catholyte was analyzed in the same manner as in Example 1. The results are as follows:

conversion of methyl acrylate, 100%; conversion of heptanal, 7%; selectivity for 4-n-hexyl-4-butanolide based on methyl acrylate, 2.9%; selectivity for 4-n-hexyl-4-butanolide based on heptanal, 14%; current efficiency, 2.4%; and selectivity for 1-heptanol, 86% (a large amount of 1-heptanol was produced).

COMPARATIVE EXAMPLE 2

The electrolytic cell as described in Example 1 and 10 wt% sulfuric acid as an anolyte were used. As a catholyte was used a mixture of 5.23 g (72.6 mmol) of butanal, 2.15 g (25.0 mmol) of methyl acrylate, 29.0 g of water, 10.43 g (34.7 mmol) of tetraethylammonium-p-toluenesulfonate and 41.52 g of dimethylformamide as a solvent for forming a homogeneous system. The electrolysis was carried out in a homogeneous system at a catholyte temperature of 30° to 32° C. and a current density of 10.2 A/dm$^2$. The electrolysis was discontinued when the relative current quantity reached 104%. Then, the catholyte was analyzed in the same manner as in Example 1. The results are as follows.

conversion of methyl acrylate, 90%; conversion of butanal, 74%; selectivity for 4-n-propyl-4-butanolide based on methyl acrylate, 52%; selectivity for 4-n-propyl-4-butanolide based on butanal, 22%; and current efficiency, 45%.

The intended product, 4-n-propyl-4-butanolide, was separated from the catholyte as follows. To the catholyte was added 200 g of water and then 100 ml of ether. The resulting mixture was thoroughly shaked to distribute 4-n-propyl-4-butanolide into the ether layer, so that extraction of 4-n-propyl-4-butanolide with ether was effected. The above operation of extraction of 4-n-propyl-4-butanolide was repeated five times each with 100 ml of ether.

COMPARATIVE EXAMPLE 3

In substantially the same manner as in Example 1, the electrolysis was carried out except that a mixture of 5.23 g (72.6 mmol) of butanal, 2.15 mmol) of methyl acrylate, 53.7 g of water and 2.35 g of potassium dihydrogenphosphate as an inorganic electrolyte was used as a catholyte instead of the catholyte as used in Example 1. The electrolysis was discontinued when the relative current quantity reached 102%. Then, the catholyte was analyzed in the same manner as in Example 1. The results are as follows:

conversion of methyl acrylate, 85%; conversion of butanal, 38%; selectivity for 4-n-propyl-4-butanolide based on methyl acrylate, 48%; selectivity for 4-n-propyl-4-butanolide based on butanal, 37%; current efficiency, 40%; selectivity for 1-butanol, 53%; selectivity for methyl propionate, 9%; and selectivity for dimethyl adipate, 1%.

COMPARATIVE EXAMPLE 4

In substantially the same manner as in Example 8, the electrolysis was carried out except that a mixture of 8.61 g (75.5 mmol) of heptanal, 2.16 g (25.1 mmol) of methyl acrylate, 52.8 g of water and 2.37 g of potassium dihydrogenphosphate as an inorganic electrolyte was used as a catholyte instead of the catholyte as used in Example 8. The electrolysis was discontinued when the relative current quantity reached 105%. Then, the catholyte was analyzed in the same manner as in Example 1. The results are as follows:

conversion of methyl acrylate, 83%; conversion of heptanal, 5%; selectivity for 4-n-hexyl-4-butanolide based on methyl acrylate, 5%; selectivity for 4-n-hexyl-4-butanolide based on heptanal, 26%; current efficiency, 4%; selectivity for 1-heptanol, 74%; selectivity for methyl propionate, 82%; and selectivity for dimethyl adipate, 10%.

What is claimed is:

1. A process for the preparation of a 4-butanolide compound which comprises subjecting a mixture of an acrylic ester and an aldehyde selected from the group consisting of aliphatic aldehydes having 1 to 13 carbon atoms, aromatic aldehydes and aralkyl aldehydes to electrolytic reduction, said mixture of the acrylic ester and the aldehyde being in the form of an aqueous emulsion comprising a water phase and an organic phase, in the presence of at least one phase-transfer catalyst selected from the group consisting of quaternary ammonium salts represented by the general formula:

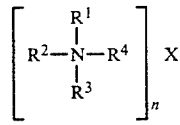

wherein X stands for an acid radical, n stands for an integer corresponding to the valence of X, and $R^1$, $R^2$, $R^3$ and $R^4$ each independently stand for an alkyl group or an aralkyl group, provided that, when said aldehyde is an aliphatic aldehyde having 5 to 13 carbon atoms, an aromatic aldehyde or an aralkyl aldehyde, the total number of carbon atoms in $R^1$, $R^2$, $R^3$ and $R^4$ of the quaternary ammonium ion moiety is 12 to 30, said total number of carbon atoms is $R^1$, $R^2$, $R^3$ and $R^4$ being calculated by the equation n×(carbon number in $R^1$+carbon number in $R^2$+carbon number in $R^3$+carbon number in $R^4$)/n, and quaternary phosphonium salts in an electrolytic cell provided with at least one pair of anode and cathode, said cathode being made of lead or a lead alloy.

2. A process according to claim 1, wherein said acrylic ester is a lower alkyl ester of acrylic acid.

3. A process according to claim 2, wherein said lower alkyl ester of acrylic acid is methyl acrylate.

4. A process according to claim 1, wherein said organic phase is present in said aqueous emulsion in a volume ratio of 0.05 to 0.5 relative to the total volume of said aqueous emulsion.

5. A process according to claim 1, wherein said electrolytic reduction is carried out in a two-compartment electrolytic cell partitioned by a diaphragm.

6. A process according to claim 1, wherein said aldehyde is employed in a molar ratio of 1 to 10 relative to said acrylic ester.

7. A process according to claim 1, wherein said electrolytic reduction is carried out in the presence of at least one inorganic electrolyte in addition to said at least one phase-transfer catalyst.

8. A process according to claim 7, wherein said inorganic electrolyte is at least one compound selected from the group consisting of sulfuric acid, phosphoric acid, an alkali metal sulfate, an alkali metal hydrogensulfate, a dialkali metal hydrogenphosphate and an alkali metal dihydrogenphosphate.

9. A process according to claim 1, wherein said aldehyde is an aliphatic aldehyde having up to 4 carbon atoms and said phase-transfer catalyst is a quaternary ammonium salt represented by the general formula:

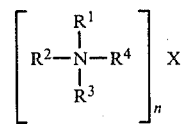

wherein X stands for an acid radical, n stands for an integer corresponding to the valence of X, and $R^1$, $R^2$, $R^3$ and $R^4$ each independently stand for an alkyl group or an aralkyl group, provided that the total number of carbon atoms in $R^1$, $R^2$, $R^3$ and $R^4$ is 4 to 20, said total number of carbon atoms in $R^1$, $R^2$, $R^3$ and $R^4$ being calculated by the equation n×(carbon number in $R^1$+carbon number in $R^2$+carbon number in $R^3$+carbon number in $R^4$)/n.

10. A process according to claim 9, wherein each of $R^1$, $R^2$, $R^3$ and $R^4$ is an alkyl group and the total number of carbon atoms in $R^1$, $R^2$, $R^3$ and $R^4$ is 4 to 16.

11. A process according to claim 10, wherein at least one of $R^1$, $R^2$, $R^3$ and $R^4$ is an alkyl group selected from the group consisting of a methyl group, an ethyl group, a propyl group and a butyl group.

12. A process according to claim 1, wherein said aldehyde is an aliphatic aldehyde having 5 to 13 carbon atoms, an aromatic aldehyde or an aralkyl aldehyde, and said phase-transfer catalyst is a quaternary ammonium salt represented by the general formula:

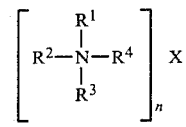

wherein X stands for an acid radical, n stands for an integer corresponding to the valence of X, and $R^1$, $R^2$, $R^3$ and $R^4$ each independently stand for an alkyl group or an aralkyl group, provided that the total number of carbon atoms in $R^1$, $R^2$, $R^3$ and $R^4$ is 12 to 20, said total number of carbon atoms in $R^1$, $R^2$, $R^3$ and $R^4$ being calculated by the equation n×(carbon number in $R^1$+carbon number in $R^2$+carbon number in $R^3$+carbon number in $R^4$)/n.

13. A process according to claim 12, wherein $R^1$, $R^2$, $R^3$ and $R^4$ each independently represent an alkyl group and at least three of them each independently represent an alkyl group having at least three carbon atoms.

14. A process according to claim 13, wherein at least one of $R^1$, $R^2$, $R^3$ and $R^4$ is an alkyl group selected from the group consisting of a propyl group and a butyl group.

15. A process according to claim 14, wherein each of $R^1$, $R^2$, $R^3$ and $R^4$ is a butyl group.

16. A process according to claim 7, wherein said aldehyde is an aliphatic aldehyde having 5 to 13 carbon atoms, aromatic aldehyde or an aralkyl aldehyde, and said phase-transfer catalyst is a quaternary ammonium salt represented by the general formula:

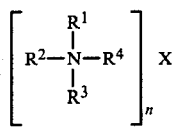

wherein X stands for an acid radical, n stands for an integer corresponding to the valence of X, and $R^1$, $R^2$, $R^3$ and $R^4$ each independently stand for an alkyl group or an aralkyl group, provided that the total number of carbon atoms in $R^1$, $R^2$, $R^3$ and $R^4$ is 12 to 30, said total number of carbon atoms in $R^1$, $R^2$, $R^3$ and $R^4$ being calculated by the equation n×(carbon number in $R^1$+carbon number in $R^2$+carbon number in $R^3$+carbon number in $R^4$)/n, or a quaternary phosphonium salt.

17. A process according to claim 16, wherein said quaternary ammonium salt is employed in an amount of 0.1 to 50 mol % based on the amount of said acrylic ester or said aldehyde, whichever is less in amount employed.

18. A process according to claim 16, wherein said quaternary phosphonium salt is employed in an amount of 0.1 to 50 mol % based on the amount of said acrylic ester or said aldehyde, whichever is less in amount employed.

19. A process according to claim 9, 12 or 16, wherein said acid radical is a sulfate ion, sulfonate ion, phosphate ion, hydrogenphosphate ion, dihydrogenphosphate ion, hydrogensulfate ion or halide ion.

20. A process according to claim 17, wherein said acid radical is a sulfate ion, p-toluenesulfonate ion, phosphate ion, hydrogenphosphate ion, dihydrogenphosphate ion, or hydrogensulfate ion.

* * * * *